United States Patent [19]
Berry et al.

[11] Patent Number: 5,583,113
[45] Date of Patent: Dec. 10, 1996

[54] USE OF A DIRECT-ACTING THROMBIN INHIBITOR FOR THE MANUFACTURE OF A MEDICINAL PRODUCT HAVING THROMBOLYTIC ACTIVITY

[75] Inventors: Christopher Berry, Champigny S/Marne; Patrice Ferrari, Bois d'Arcy, both of France

[73] Assignee: Synthelabo, Le Plessis Robinson, France

[21] Appl. No.: 387,382

[22] Filed: Feb. 13, 1995

Related U.S. Application Data

[63] Continuation of Ser. No. 114,067, Aug. 31, 1993, abandoned.

[30] Foreign Application Priority Data

Sep. 11, 1992 [FR] France .................................. 92 10833

[51] Int. Cl.$^6$ .......................... A61K 38/00; A01N 37/36; A61K 31/615
[52] U.S. Cl. ............................................. 514/18; 514/166
[58] Field of Search ........................................ 514/18, 166

[56] References Cited

U.S. PATENT DOCUMENTS

| 4,258,192 | 3/1981 | Okamoto et al. ...................... | 546/166 |
|---|---|---|---|
| 4,318,904 | 3/1982 | Shaw et al. ............................. | 424/177 |
| 4,929,602 | 5/1989 | Harker et al. ............................ | 514/18 |

FOREIGN PATENT DOCUMENTS 02750  3/1991  WIPO.

OTHER PUBLICATIONS

S. Budavari et al., (EDS.), The Merck Index, 11th Ed., 1989, p. 123, No. 804.
S. Budavari et al., (EDS.), The Merck Index, 11th Ed., 1989, p. 1220, No. 7702.
A. Chiu et al., "Inhibition of the thrombin–platelet reactions by DuP 714", Biochemical & Bio–Physical Research Communications, vol. 179, No. 3, Sep. 30, 1991, pp. 1500–1508.
Kettner et al. J. Biol. Chem., vol. 265 pp. 18289–18297 1990.
Collen et al., J. Lab. Clin. Med. vol. 99 pp. 76–83 1982.
Kikumoto et al., Biochem, vol. 23, pp. 85–90, 1984.
Schneider, Thrombosis Research vol. 64, p. 677 (1991).
Agnelli et al, Blood vol. 76 p. 2030 (1990).

*Primary Examiner*—Marian C. Knode
*Assistant Examiner*—Sheela J. Huff
*Attorney, Agent, or Firm*—Jacobson, Price, Holman & Stern, PLLC

[57] ABSTRACT

A method for inducing thrombolysis, which method comprises administering to a patient a thrombolytically effective amount of a thrombin inhibitor which acts at the active site of thrombin, in the absence of exogenous plasminogen activator. The inhibitor is preferably argatroban, D-Phe-Pro-Arg-chloromethyl ketone, or Ac-(D-Phe)-Pro-boro-Arg-OH.

2 Claims, No Drawings

USE OF A DIRECT-ACTING THROMBIN INHIBITOR FOR THE MANUFACTURE OF A MEDICINAL PRODUCT HAVING THROMBOLYTIC ACTIVITY

This application is a continuation of application Ser. No. 08/114,067, filed Aug. 31, 1993 now abandoned.

The present invention relates to the use of a direct acting thrombin inhibitor for the preparation of a medicinal product having thrombolytic activity.

BACKGROUND OF THE INVENTION

Compounds which inhibit thrombin by interaction with the active site of this protease are used or are being developed as antithrombotic agents. Examples of such compounds include argatroban (Okamoto S. et al. Biochem. Biophys. Res. Commun. 101, 440, 1981 inter alia), PPACK (Kettner C. A. and Shaw E. N., Thromb. Res. 14, 969, 1979 inter alia), DUP 714 (Kettner C. A. et al J. Biol. Chem. 265, 18289, 1990 inter alia) and hirudins (Rydel T. J. et al. Science vol. 249, page 277, July 1990 inter alia).

In the case of myocardial infarction, arterial or venous thrombosis or pulmonary embolism, thrombin inhibitors can accelerate lysis and prevent reocclusion after treatment with an exogenous thrombolytic agent such as recombinant plasminogen activator (rTPA) or streptokinase.

SUMMARY OF THE INVENTION

The Applicant has studied the activity of direct acting thrombin inhibitors per se, as thrombolytic agents in the absence of exogenous plasminogen activators. The invention provides a method for inducing thrombolysis, which method comprises administering to a patient a thrombolytically effective amount of a thrombin inhibitor which acts at the active site of thrombin, in the absence of exogenous plasminogen activator.

DETAILED DESCRIPTION THE INVENTION

The compounds which are usable according to the invention were studied in rats for their activity as thrombolytic agents in a model of electrical stimulation induced occlusive aortic thrombosis.

CD rats weighing 450 g to 500 g are anaesthetized with sodium pentobarbital (60 mg/kg i.p.) and the left renal artery is catheterized. Thrombosis is induced according to the method described by Hladovec (Throm. Haemosts. (1971), 26, 407–410). A segment of abdominal aorta approximately 1 cm in length is exposed between the renal artery and the iliac bifurcation, and an electromagnetic flow probe is placed around this segment to measure blood flow rate, and a bipolar electrode is placed downstream of the probe. After 15 minutes of stabilisation, a 5 mA direct current is applied for 5 minutes to the outer surface of the artery using a stimulator. When the flow rate reaches the zero value, previously determined by clamping the artery between the probe and the electrode, the time to formation of an occlusive thrombus is noted. After 5 minutes of stabilisation of the thrombus, the test compound or the vehicle is injected via the catheter as a 0.5 ml bolus followed by a 60 minute perfusion at 0.1 ml/min. The blood flow rate is recorded during the perfusion period. Thrombolysis is estimated by measuring the area under the blood flow trace, which reflects both the time to, and the extent of recanalisation. The results are expressed as a mean #standard error of the mean.

In animals receiving the vehicle, the abdominal aorta remains occluded throughout the period of administration. In contrast, direct acting thrombin inhibitors increase the area under the curve in a dose-dependent manner and rapidly restore blood flow.

The Applicant has tested, more especially, the following substances: argatroban, D-Phe-Pro-Arg chloromethyl ketone (PPACK) and Ac-(D-Phe)-Pro-boro-Arg-OH (DUP 714) with the following formula (1)

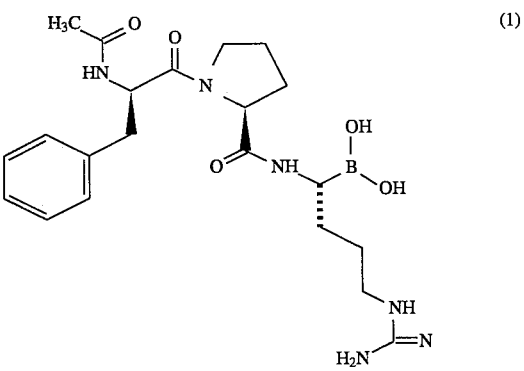

which have shown thrombolytic activity. The results are given in the table on page 4. The results of the tests show that direct acting thrombin inhibitors may be used for the manufacture of medicinal products having thrombolytic activity.

They may be used in pathologies which involve the use of a thrombolytic agent, such as myocardial infarction, peripheral arterial disease, deep vein thrombosis and pulmonary embolism.

To this end, they may be presented in all pharmaceutical dosage forms which are suited to intravenous administration,. in combination with suitable excipients, at doses that permit a daily administration of 10 to 500 mg of active substance.

TABLE

Thrombolytic Action of argatroban, PPACK and DUP 714

| Compound | Dose µg/kg + µg/kg/min | n | Area under the curve (cm$^2$ ± s.e.m.) | % Increase | Number of animals showing thrombolyis |
|---|---|---|---|---|---|
| Vehicle | — | 11 | 35.8 ± 12.5 | — | 0 |
| Argatroban | 25 + 5 | 8 | 137.5 ± 45.6 | 284 | 4# |
|  | 100 + 20 | 8 | 181.1 ± 99.6 | 406 | 3 |
|  | 200 + 40 | 8 | 460.3 ± 86.5** | 1186 | 7## |
| Vehicle | — | 8 | 43.4 ± 21.6 | — | 0 |
| PPACK | 50 + 10 | 8 | 291.7 ± 96.5 | 572 | 5# |
|  | 100 + 20 | 8 | 284.8 ± 98.9 | 556 | 5# |

TABLE-continued

Thrombolytic Action of argatroban, PPACK and DUP 714

| Compound | Dose µg/kg + µg/kg/min | n | Area under the curve (cm² ± s.e.m.) | % Increase | Number of animals showing thrombolyis |
|---|---|---|---|---|---|
| | 200 + 40 | 8 | 542.7 ± 75.2** | 1148 | 7## |
| Vehicle | — | 9 | 47.2 ± 34.0 | — | 1 |
| DUP714 | 100 + 20 | 8 | 339.7 ± 84.7* | 620 | 5## |
| | 200 + 40 | 8 | 362.3 ± 61.1* | 667 | 7## |
| | 400 + 80 | 8 | 575.3 ± 99.0** | 1118 | 8## |

*$p < 0.05$,
**$p < 0.01$ versus vehicle Dunnett's test
$p < 0.05$,
$p < 0.01$ versus vehicle Fisher's exact test

We claim:

1. A method for inducing thrombolysis in a patient suffering from a condition resulting from thrombin activation, which method comprises administering to said patient a thrombolytically effective amount of a thrombin inhibitor selected from the group consisting # of agatraban, D-Phe-Pro-Arg-chloromethylketone, and Ac-(D-Phe)-Pro-boro-Arg-OH, in the absence of exogenous plasminogen activator.

2. A method for inducing thrombolysis in a patient suffering from a condition selected from the group consisting of myocardial infarction, peripheral arterial disease, deep vein thrombosis, and pulmonary embolism, which method comprises administering to said patient, a thrombolytically effective amount of a thrombin inhibitor selected from the group consisting # of agatraban, D-Phe-Pro-Arg-chloromethylketone,and Ac-(D-Phe)-Pro-boro-Arg-OH, in the absence of exogenous plasminogen activator.

* * * * *